(12) United States Patent
Haworth

(10) Patent No.: US 11,129,701 B1
(45) Date of Patent: Sep. 28, 2021

(54) LIP IMPLANT AND ASSOCIATED SURGICAL METHOD

(71) Applicant: Steve A. Haworth, Gilbert, AZ (US)

(72) Inventor: Steve A. Haworth, Gilbert, AZ (US)

( * ) Notice: Subject to any disclaimer, the term of this patent is extended or adjusted under 35 U.S.C. 154(b) by 0 days.

(21) Appl. No.: 17/198,853

(22) Filed: Mar. 11, 2021

(51) Int. Cl.
*A61F 2/07* (2013.01)
*A61F 2/00* (2006.01)

(52) U.S. Cl.
CPC .... *A61F 2/0059* (2013.01); *A61F 2210/0057* (2013.01); *A61F 2220/0075* (2013.01)

(58) Field of Classification Search
CPC ... A61F 2/105; A61F 2017/00747; A61F 2/02
USPC ............................................. 623/15.12, 23.72
See application file for complete search history.

(56) References Cited

U.S. PATENT DOCUMENTS

| | | | |
|---|---|---|---|
| 7,008,455 B2* | 3/2006 | Raphael | A61B 17/282 623/11.11 |
| 7,329,286 B2 | 2/2008 | Raphael | |
| 7,344,566 B2* | 3/2008 | Raphael | A61B 17/282 623/11.11 |
| 7,641,688 B2 | 1/2010 | Lesh | |
| 7,998,202 B2* | 8/2011 | Lesh | A61M 29/02 623/11.11 |
| 8,052,423 B2 | 11/2011 | Alghamdi | |
| 9,271,817 B2 | 3/2016 | Dempsey et al. | |
| 9,895,211 B2 | 2/2018 | Yaremchuk | |
| 9,913,704 B1 | 3/2018 | Yaremchuk | |
| 2002/0019670 A1* | 2/2002 | Crawley | A61F 2/08 623/11.11 |
| 2003/0181928 A1* | 9/2003 | Vidlund | A61B 17/00234 606/151 |
| 2003/0195510 A1* | 10/2003 | Schaer | A61B 18/1492 606/41 |
| 2004/0073318 A1* | 4/2004 | Reinmuller | A61L 27/18 623/23.72 |
| 2005/0177234 A1* | 8/2005 | Raphael | A61B 17/282 623/11.11 |
| 2006/0058892 A1* | 3/2006 | Lesh | A61F 2/0059 623/23.72 |
| 2006/0136070 A1* | 6/2006 | Pinchuk | A61B 17/06004 623/23.72 |
| 2007/0196421 A1 | 8/2007 | Hunter et al. | |

(Continued)

FOREIGN PATENT DOCUMENTS

EP          2349080          8/2011

OTHER PUBLICATIONS

Website: https://surgisil.com/global/index.php/features/; printed pdf of website on Mar. 11, 2021; see p. 1 of attached pdf file surgisil_com_permalip.pdf.

*Primary Examiner* — Suzette J Gherbi
(74) *Attorney, Agent, or Firm* — Mark V. Loen

(57) ABSTRACT

The embodied invention is a lip implant that includes small eyelets on either end of a small diameter rod located inside, and extends beyond, the cosmetic volume of the implant. Sutures connected to eyelets on the rod ends, allow the implant to be pulled into a minimal lip cavity that is created for the implant. The implant is readily positioned by using the sutures. Only two small incisions are needed as well as the creation of a small cavity needed for the implant. The use of the embodied invention is also extended to vein implants to enhance the appearance of veins on arms, legs, or to other surfaces.

3 Claims, 8 Drawing Sheets

(56) References Cited

U.S. PATENT DOCUMENTS

| | | | |
|---|---|---|---|
| 2008/0058928 A1* | 3/2008 | Raphael | A61B 17/282 |
| | | | 623/11.11 |
| 2009/0048684 A1* | 2/2009 | Lesh | A61F 2/0059 |
| | | | 623/23.72 |
| 2010/0137679 A1* | 6/2010 | Lashinski | A61B 17/0401 |
| | | | 600/37 |
| 2011/0264215 A1* | 10/2011 | Raphael | A61F 2/0059 |
| | | | 623/11.11 |
| 2013/0012765 A1* | 1/2013 | Vemuri | A61F 2/0045 |
| | | | 600/30 |
| 2017/0304039 A1* | 10/2017 | Eaves, III | A61F 2/0059 |
| 2018/0092736 A1* | 4/2018 | Lee | A61B 17/06166 |
| 2018/0098850 A1* | 4/2018 | Rafiee | A61F 2/2451 |
| 2019/0201203 A1* | 7/2019 | Jiang | A61F 2/30756 |
| 2020/0000971 A1* | 1/2020 | Sakamoto | A61L 27/56 |
| 2021/0085464 A1* | 3/2021 | Cabiri | A61F 2/2442 |

* cited by examiner

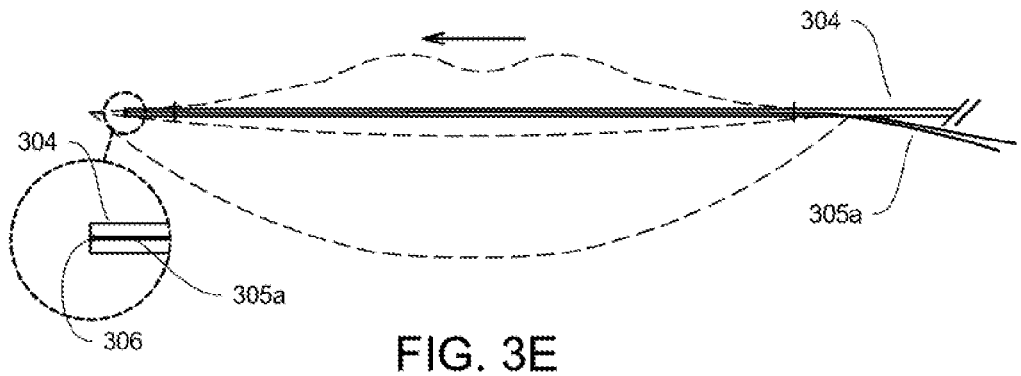
FIG. 3F
FIG. 3E
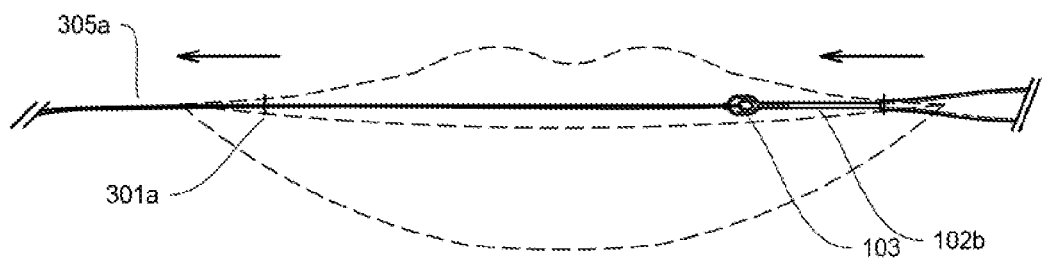
FIG. 3G
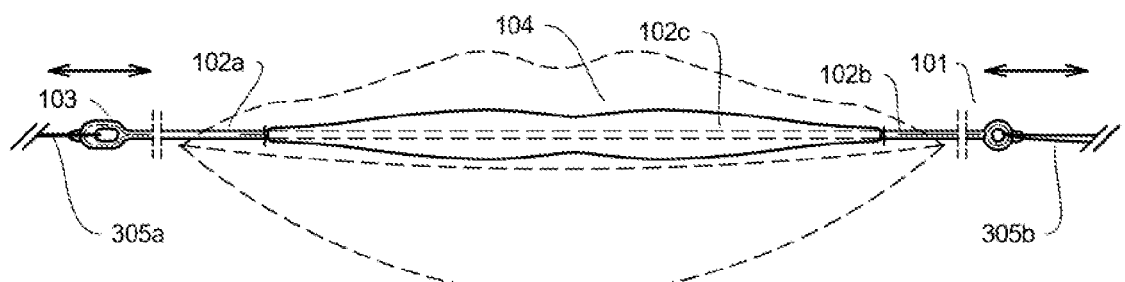
FIG. 3H

LIP IMPLANT AND ASSOCIATED SURGICAL METHOD

CROSS REFERENCE TO RELATED APPLICATIONS

Not applicable

STATEMENT OF FEDERALLY SPONSORED RESEARCH OR DEVELOPMENT

Not applicable.

BACKGROUND OF THE INVENTION

(1) Field of the Invention

This invention is directed to cosmetic implants and surgical methods to insert them into the tissue of a patient.

(2) Description of Related Art

This applicant is related to cosmetic implants and the surgical method required to implant in a patient's skin that avoids implant damage and minimizes tissue damage.

Cosmetic implants are a common personal enhancement operation. There were about 32,000 lip augmentation procedures in 2019 according to Plastic Surgery Statistics Report by ASPS National Clearinghouse of Plastic Surgery Procedural Statistics. This does not include lip filling procedures.

US publication number 20110264215 describes a lip implant which may be used for lip augmentation or enhancement, and a surgical procedure. The implant is made from silicone, expanded PTFE, urethane, and a biocompatible polymer. To insert the implant, the medical procedure is to make incisions at the commissure (corner of lip) and utilize iris scissors to dissect a tunnel (or cavity) halfway from each corner. The iris scissors are then manipulated to increase the tunnel diameter completely across the lip. An instrument (curved or straight clamp) is then passed completely through the tunnel and is used to clamp one end of the implant. The implant is then pulled into the center of the tunnel and the clamp is released. The incisions are then sutured and an antibiotic ointment is applied to the suture area.

The act of creating a long tunnel, and the multiple instruments needed to pass through the lip, create significant trauma to the lip tissue. Side effects seen by patients are redness and increased sensitivity in the injected areas, slight bleeding at the injections' site. Sometimes, side effects are more serious, such as lip asymmetry, lumps, ongoing swelling and bruising, ulceration, or an allergic reaction.

Also, the current art surgical methods utilize a clamp to pull the implant into the long tunnel that cause various problems with the soft implant. The ends of the current art implants tend to break off. This leaves the broken implant with a missing taper and is cosmetically unappealing. Also, the clamp has teeth which damage the implant end, and will often leave teeth marks or protrusions that can be felt or seen. These issues frequently cause high dissatisfaction with the implant and require a second corrective surgery. This is a known problem without a solution.

Similarly, a long skin implant that is used to create the appearance of a vein has similar trauma and implant end damage issues.

It is desirable to design an implant that minimizes the damage to the soft tissue of the lip, especially swelling or bruising, and enhance tissue healing and recovery. Also, it is desirable to have a surgical method that does not damage or mar the implant. To that end, it is also desirable to improve the surgical procedure as well, so that the implant is undamaged when positioned.

BRIEF STATEMENT OF THE INVENTION

The embodied invention is a lip implant that includes small eyelets on either end of a small diameter rod located inside, and extends beyond, the cosmetic volume of the implant. Sutures connected to eyelets on the rod ends, allow the implant to be pulled into a minimal lip cavity that is created for the implant. The implant is readily positioned by using the sutures. Only two small incisions are needed as well as the creation of the small cavity needed for the implant.

The use of the embodied invention is also extended to vein implants to enhance the appearance of veins on arms, legs, or to other surfaces.

BRIEF DESCRIPTION OF THE FIGURES

FIGS. 3A-3K highlight the surgical method to insert and position the lip implant.

DETAILED DESCRIPTION OF THE INVENTION

The embodied invention addresses the need to minimize tissue damage by creating a minimal diameter lip cavity and reducing its length. Also, the lip implant position is improved by the shorter cavity, avoiding any mis-positioning during surgery.

Figure 1:
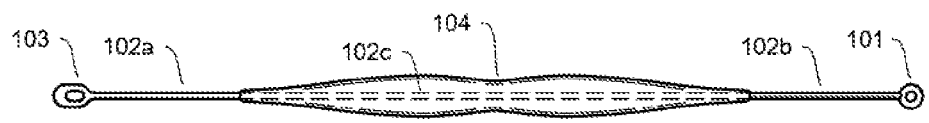
FIG. 1 shows a lip implant with a moderate hourglass shape.

FIG. 1 shows a lip implant with an end tapered, cosmetically shaped, center volume 104.

An elongated central rod comprises an inner rod 102c, two outer rods 102a,b, and two eyelets 101, 103 on the ends of the outer rods. The implant is preferably made from two different hardness of medical grade silicone. The central rod is preferably made with a 20-30 durometer (Shore A Durometer Scale), to have strength and moderate stretchability, and a softer 0.1 to 5 durometer (Shore A Durometer Scale) cosmetically shaped center volume. A higher durometer cosmetic shape will not feel natural or will not be flexible enough to fill the lip cavity created in surgery. The two different durometers provide the strength that is needed to pull the entire lip implant into lip tissue, and it also allows a softer implant which fills up the lip in a manner that makes it unlikely to be felt when firmly implanted in lip tissue.

Typically, the lip implant is about 100-110 mm long, and the cosmetic volume 50-65 mm long, which depends upon the desired effect on the lip. The cosmetic volume is about 3 to 12 mm in diameter, again depending upon the desired effect to a lip. The central rod is about 0.8 to 1.6 mm in diameter.

The cosmetically shaped volume 104 is symmetrical about the central rod axis and centered on the central rod.

Typically, the eyelets rings are about 2 to 3 mm outside diameter, with a thickness that matches the central rod diameter. The eyelet inner opening must be larger than the suture diameter being used. The tensile strength of the rod is typically 600-1000 psi. Preferably, at least one eyelet is slightly elongated to allow higher strength for pulling the lip implant into the lip cavity. However, this is not a requirement. Only one elongated eyelet is illustrated for simplicity of illustration. A preferred embodiment is to have an elongated eyelet on both ends.

The cosmetic volume naturally bonds to the central rod due to the similarity of using medical grade silicone and natural adhesion of silicone to itself. Generally, no epoxy is required to bond the cosmetic volume to the central rod.

Medical grade silicone means that a silicone is used that meets the requirements for long term use inside a human body.

Figure 2:
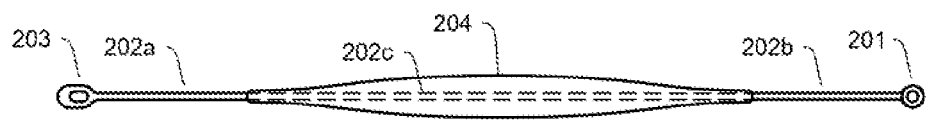
FIG. 2 shows a similar implant with a tapered cylindrical shape.

Similarly to FIG. 1, FIG. 2 shows a second lip implant with a tapered ends, a cosmetically shaped center volume 204, a central rod 202a,b,c, and two eyelets 201, 203. The only difference being the cosmetic volume which is illustrated as two cones with the bases joined. The shaped cosmetic volume and central rod function the same as FIG. 1. In some patients, the upper lip may be modified by a shape as in FIG. 1, and the lower lip modified by a shape as in FIG. 2.

Other types of cosmetic shapes could equally be used.

FIGS. 3A-3I illustrate the various steps of inserting the lip implant into the lip tissue. Both the upper and lower lips utilize the same steps.

Figure 3A:
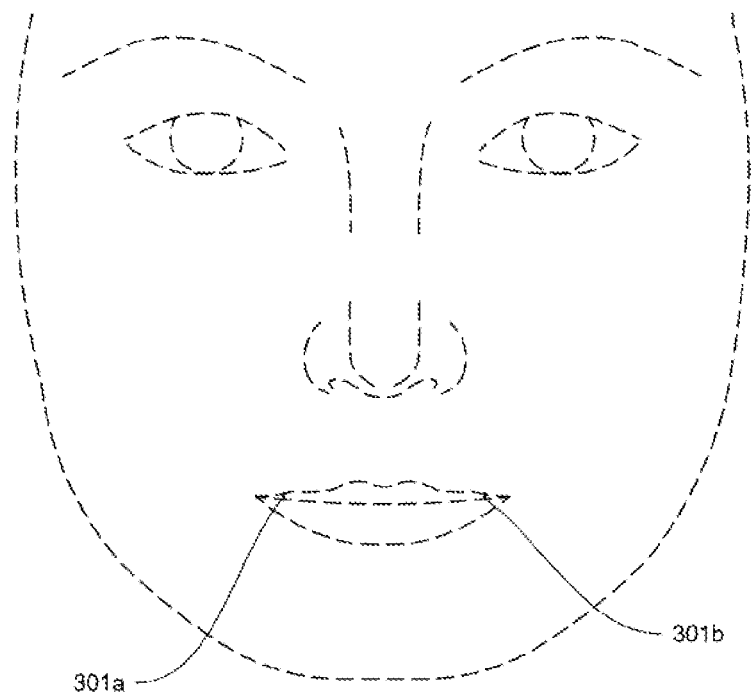

FIG. 3A shows the incision places 301a,b which are preferably not on the commissure of the lip. Typically, they are positioned about 2-3 mm inwardly from the commissure. The incisions can be 3 to 10 mm long, depending up on the size of the implant. However, the cosmetic volume will stretch as it is pulled into the lip, and the length of the incision can therefore be smaller than the diameter of the cosmetic volume. This is a distinct advantage of the embodied invention.

Figure 3B:
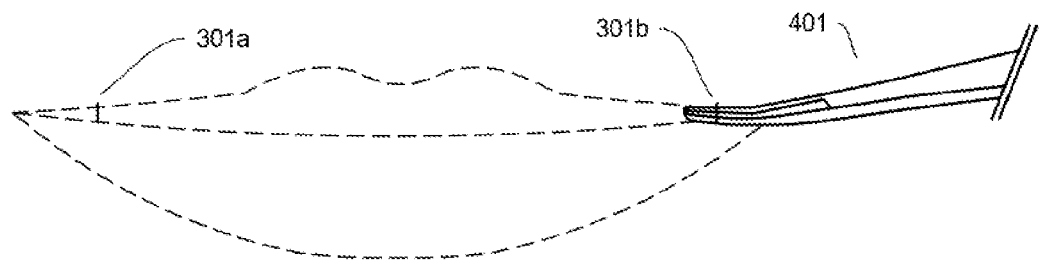

FIG. 3B shows the use of a surgeon scissors 401 to create an initial entry tunnel in the lip tissue.

Figure 3C:
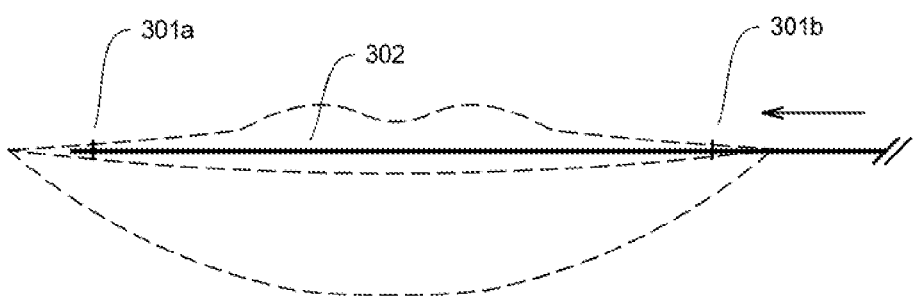

FIG. 3C shows the use of a cannula 302 (such as a 20 gauge) to create an initial tunnel through the lip tissue.

Figure 3D:
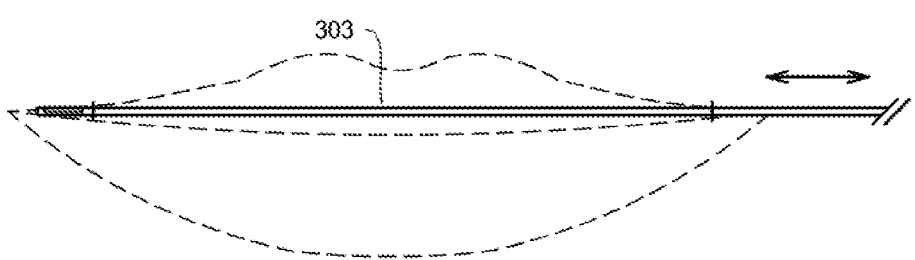

FIG. 3D shows an larger diameter cannula 303 (such as a liposuction and filtration cannula) to increase the cavity size. This may be an optional step if the first cannula creates a large enough cavity.

FIG. 3E shows a suture placement rod 304 that pushes a left side suture 305a through the lip cavity. The suture 305a is captured in an end groove 306 as illustrated in FIG. 3F. Right and left sutures are from the surgeon's perspective.

In FIG. 3G, the suture placement rod has been removed and the left side suture 305a has been looped through the eyelet 103 and is tied there. The lip implant as shown in FIG. 1 is being pulled through in this illustration, and the left eyelet 103 is shown. Preferably, the surgeon will stretch pull the left end of the cosmetic volume to the left incision 301a, manually hold that end in position, and then slowly release the stretch to allow the implant to slide into the cavity. However, this is not a requirement.

In FIG. 3H, the lip implant is inside the lip cavity, and the left and right sutures 305a,b are used to center the implant between the incisions. The surgeon will also manipulate the lip tissue to remove any pinching of the lip tissue, which will insure proper positioning of the lip insert between the two incisions. Without tension on the eyelets, the implant is highly flexible and will fill the cavity created by the surgeon.

Figure 3I:
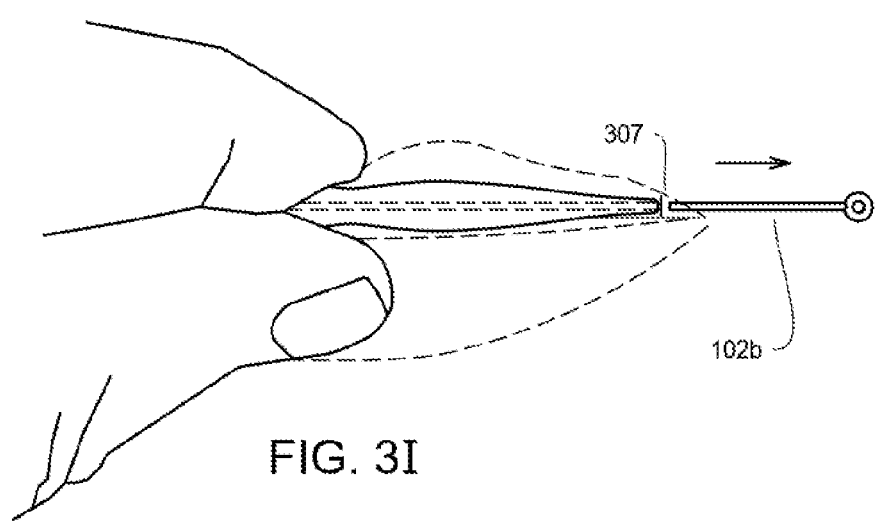

In FIG. 3I, the implant is held in place the surgeon and a scalpel is used to cut 307 the right outer rod 102b, along with the right eyelet 101, off the lip implant. Similarly, the left outer rod and left eyelet are cut away (not shown).

Figure 3J:
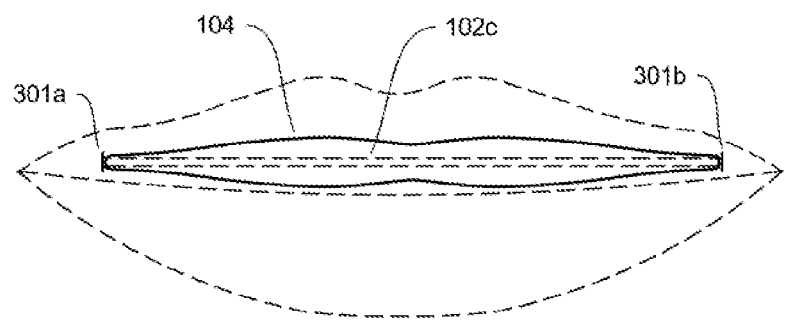

In FIG. 3J, the remaining part of limp implant (the inner rod 102c and the cosmetic volume 104) is shown with the eyelets and outer rods removed. The outer rods are cut very flush with the two ends of the cosmetic volume. The flush cut is important to avoid infections on the ends of the remaining part of the lip implant. The surgeon will manipulate the lip tissue to make a satisfactory cut so that the inner rod will not significantly protrude.

The incisions are very small and often do not need to be closed up by sutures. However, the larger diameter implants that require longer incisions may need to be stitched up.

Figure 3K:
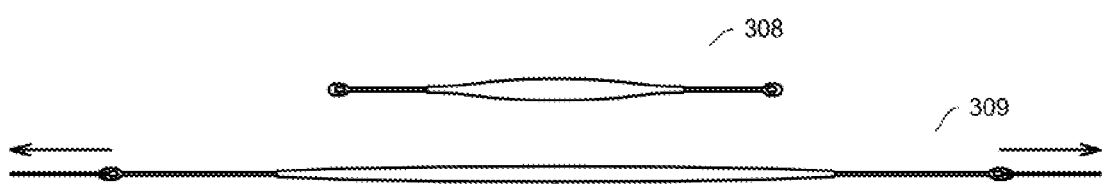

FIG. 3K illustrates how the implant will stretch, when manually pulled by sutures that are tied to the two eyelets. An unstretched implant 308 and a stretched implant 309 are shown. In this case, the illustrated stretch is about two times the unstretched length. The implant naturally stretches uniformly over its length. This is primarily due to the central rod stretching uniformly, and the cosmetic volume is softer and well attached to the central rod. The cosmetic volume will typically reduce in diameter, as already mentioned, by about ⅔ in this case. This characteristic of the implant makes surgery, and positioning of the implant, simpler. Also, the implant has a natural characteristic of filling up the surgical tunnel evenly when being released from stretching and makes positioning easier. These features of the implant are a distinct advantage of the embodied invention.

Figure 4:
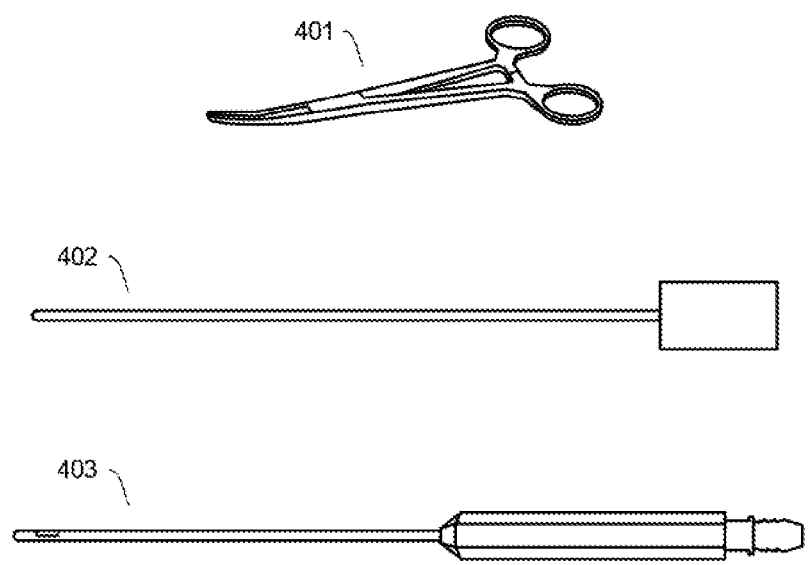
FIG. 4 shows various surgical instruments used to create a cavity in the lip.

In FIG. 4, various surgeon tools are highlighted. Surgery scissors 401, a small diameter cannula 402 and a larger diameter cannula with suction 403 are typical surgeon tools as mentioned in previous figures. Typically, a surgeon will begin with surgical scissors to create a cavity opening, and then use increasing diameter cannulas to create the needed elongated cavity.

Figure 5A:
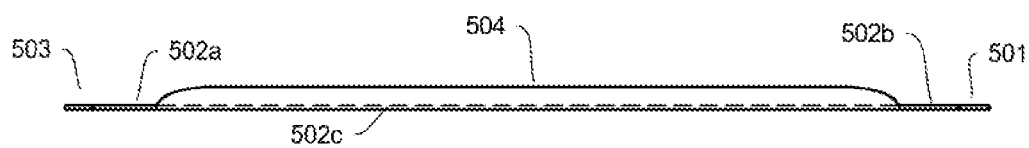
FIGS. 5A-5C show a side view and a top view of a vein implant.
Figure 5B:
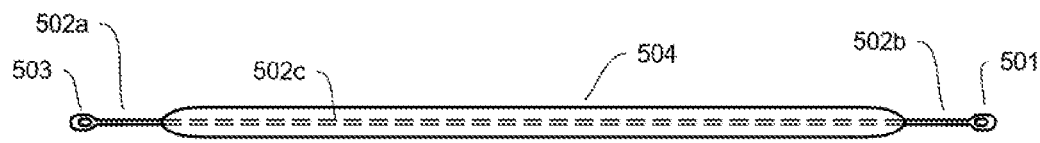
Figure 5C:

FIGS. 5A-5C show another embodied implant design. Similar to FIG. 1, a vein implant is shown with an end tapered cosmetic volume 504, with an central rod comprising an inner rod 502c, two outer rods 502a,b, and two eyelets 501, 503 on the ends of the outer rods. In this case, the central rod is located just inside of the flat surface of the cosmetic volume. Equally it could be centered in the cosmetic volume. The curved shape of the implant as shown in FIG. 5C is created by the surgeon's manipulation of the skin, and the implant is not designed with any curvature. This implant is also highly flexible and will fill the cavity created by the surgeon.

The operation to install the vein implant is the same as the lip implant. The only matter is how to create a non-straight cavity for the curved vein implant. Preferably, the surgeon will mark the position and path of the vein on the arm, and after the two incisions are made, the surgeon then uses the scissors and cannulas to create the curved cavity by following the markings and manipulating the skin tissue. The surgeon will also place the 'flat side down' so that the curved portion is pressing against the patient's outermost skin.

Figure 6:
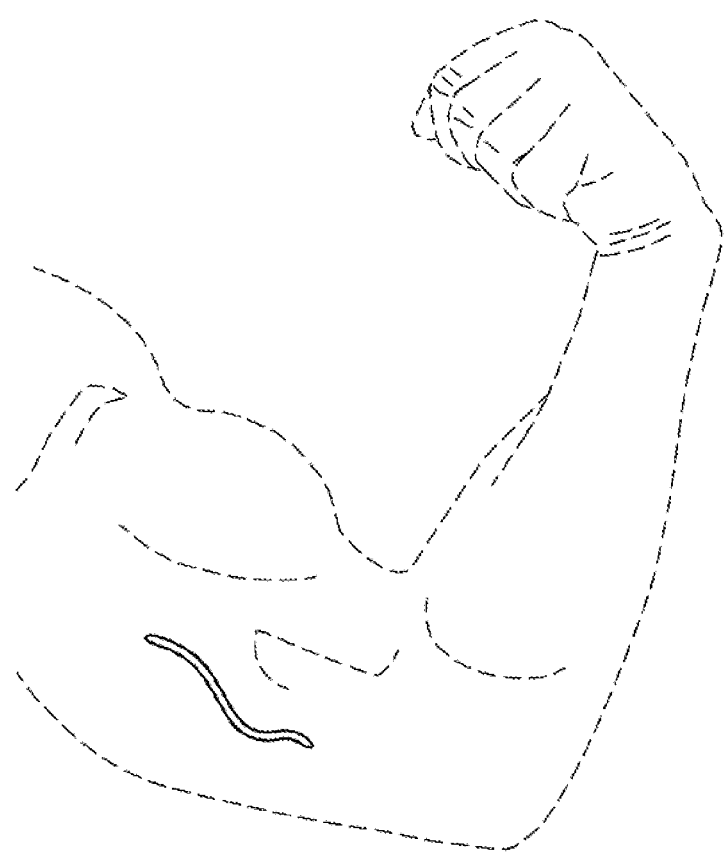
FIG. 6 shows a current art instrument for pulling a lip implant through the lip cavity.

FIG. 6 shows the skin (vein) implant on the inside skin of an arm. The use of the embodied invention is also extended to vein implants to enhance the appearance of veins among body builders such as arms or legs, or others who wish cosmetic implants on other surfaces, such as on a penile shaft.

Figure 7:
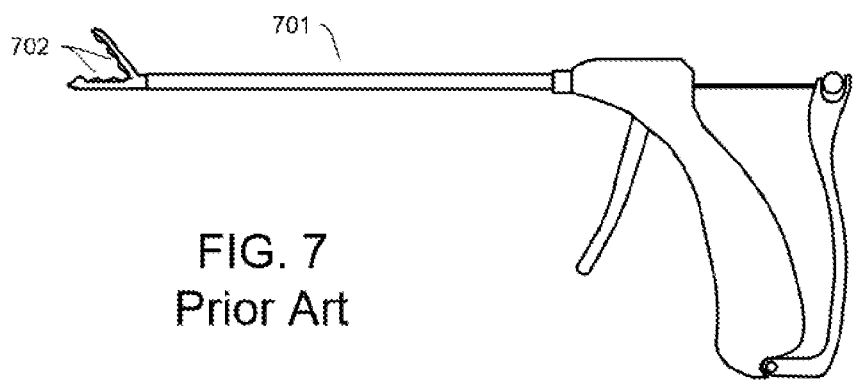
FIG. 7 shows where a vein implant could be used.

FIG. 7 shows a prior art tendon puller forceps 701 that is currently used in implants. For the conceived invention this tool is not used.

While various embodiments of the present invention have been described, the invention may be modified and adapted to various operational methods to those skilled in the art. Therefore, this invention is not limited to the description and figure shown herein, and includes all such embodiments, changes, and modifications that are encompassed by the scope of the claims.

I claim:

1. A lip implant comprising:
A) a central rod having an inner rod and two rod ends,
B) an eyelet attached to each said rod end,
C) a cosmetic volume that is attached and centered on said inner rod,
D) said cosmetic volume is radially symmetric to said inner rod and symmetric to a middle of said inner rod,
E) said cosmetic volume has tapered ends,
F) said cosmetic volume and said central rod are made from silicone,
G) said cosmetic volume having a durometer of 0.1 to 5 on a durometer A scale, and
H) said central rod having a durometer of 20 to 30 on a durometer A scale,
I) whereby said rod ends are removable during surgery, and
J) said lip implant is surgically stretchable when pulled into a lip cavity.

2. An elongated skin implant comprising:
A) a central rod having an inner rod and two rod ends,
B) an eyelet attached to each said rod end,
C) a cosmetic volume that is attached and centered on said inner rod,
D) said cosmetic volume is an elongated half circle,
E) said elongated half circle having a flat surface,
F) said cosmetic volume has tapered ends,
G) said cosmetic volume and said central rod are made from silicone,
H) said cosmetic volume having a durometer of 0.1 to 5 on a durometer A scale, and
I) said central rod having a durometer of 20 to 30 on a durometer A scale.

3. A surgical method for placing a lip implant comprising:
A) providing a lip implant further comprising:
a) a central rod having a inner rod and two rod ends,
b) a cosmetic volume that is radially symmetric to said inner rod and symmetric to a middle of said inner rod,
c) an eyelet attached to each said rod end,
d) said cosmetic volume and said central rod are made from silicone,
e) said cosmetic volume having a durometer of 0.1 to 5 on a shore durometer A scale, and
f) said central rod having a durometer of 20 to 30 on a shore durometer A scale,
B) making two incisions on a patient lip,
C) creating a cavity between said two incisions,
D) passing a first suture through said cavity,
E) attaching said first suture to a first eyelet of said lip implant,
F) attaching a second suture to a second eyelet of said lip implant,
G) pulling said first suture to place said lip implant into said cavity,
H) said lip implant is stretched when pulled into said cavity, and
I) cutting off said two rod ends from said central rod.

* * * * *